United States Patent
Robbins et al.

(10) Patent No.: US 12,396,798 B2
(45) Date of Patent: Aug. 26, 2025

(54) PROBE SHIELD

(71) Applicant: Bard Access Systems, Inc., Salt Lake City, UT (US)

(72) Inventors: Tab Robbins, Layton, UT (US); Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/030,026

(22) Filed: Sep. 23, 2020

(65) Prior Publication Data

US 2021/0100625 A1    Apr. 8, 2021

Related U.S. Application Data

(60) Provisional application No. 62/910,263, filed on Oct. 3, 2019.

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/4444* (2013.01);
(Continued)

(58) Field of Classification Search
CPC ... A61B 8/4444; A61B 17/3403; A61B 34/20; A61B 8/0841; A61B 2017/3413;
(Continued)

(56) References Cited

U.S. PATENT DOCUMENTS

2002/0123689 A1    9/2002 Furia
2011/0087106 A1*   4/2011 Ridley ................ A61B 8/0833
                                                    600/461
(Continued)

FOREIGN PATENT DOCUMENTS

EP       2347717 A1    7/2011
JP     2000245732 A    9/2000
(Continued)

OTHER PUBLICATIONS

PCT/US2020/52288 filed Sep. 23, 2020 International Search Report and Written Opinion dated Dec. 7, 2020.
(Continued)

*Primary Examiner* — Jeffrey G Hoekstra
*Assistant Examiner* — Michael Yiming Fang
(74) *Attorney, Agent, or Firm* — Rutan & Tucker LLP

(57) ABSTRACT

Disclosed herein is a needle shield for an ultrasound probe. The needle shield fits closely with an ultrasound probe head, and any associated structures, and prevents accidental damage from needle punctures and the like. Further the needle shield includes a guide wedge that allows a user to stabilize the probe at an angle relative to the skin surface. This allows perpendicular needle access to the target vessel without the probe obstructing the needle. Further the needle shield includes an acoustic lens to modify the acoustic beam and compensate for the angle position of the probe head.

21 Claims, 5 Drawing Sheets

(51) Int. Cl.
*A61B 8/08* (2006.01)
*A61B 17/34* (2006.01)
*G10K 11/16* (2006.01)

(52) U.S. Cl.
CPC .......... *A61B 17/3403* (2013.01); *G10K 11/16* (2013.01); *A61B 2017/3413* (2013.01); *A61B 2034/2063* (2016.02)

(58) Field of Classification Search
CPC ...... A61B 2034/2063; A61B 2090/378; A61B 8/00; G10K 11/16; G10K 11/02; G10K 11/30; A61N 7/00
See application file for complete search history.

(56) References Cited

U.S. PATENT DOCUMENTS

| | | | | |
|---|---|---|---|---|
| 2011/0313293 | A1* | 12/2011 | Lindekugel | A61B 8/44 600/461 |
| 2012/0165679 | A1* | 6/2012 | Orome | A61B 5/150748 600/461 |
| 2014/0088430 | A1* | 3/2014 | Poland | A61B 8/0841 600/447 |
| 2015/0245872 | A1* | 9/2015 | Hagy | A61B 8/4422 600/424 |
| 2015/0335350 | A1* | 11/2015 | Shikata | A61B 17/3403 600/443 |
| 2017/0128042 | A1* | 5/2017 | Desai | A61B 8/4281 |
| 2018/0125449 | A1 | 5/2018 | Mauldin, Jr. et al. | |
| 2020/0069283 | A1* | 3/2020 | Willis | A61B 90/39 |
| 2021/0236862 | A1* | 8/2021 | Eliason | A61N 5/062 |

FOREIGN PATENT DOCUMENTS

| | | | | |
|---|---|---|---|---|
| JP | 2018023609 | A | 2/2018 | |
| JP | 2019072369 | A | 5/2019 | |
| KR | 20190031732 | A | 3/2019 | |
| WO | 2006129084 | A1 | 12/2006 | |
| WO | 2013/188833 | A2 | 12/2013 | |
| WO | WO-2015106089 | A1 * | 7/2015 | ............... A61B 8/44 |
| WO | WO-2017094949 | A1 * | 6/2017 | ............. A61H 39/08 |

OTHER PUBLICATIONS

EP 20872368.4 filed Apr. 21, 2022 Extended European Search Report dated Nov. 30, 2023.

* cited by examiner

PROBE SHIELD

PRIORITY

This application claims the benefit of priority to U.S. Provisional Application No. 62/910,263, filed Oct. 3, 2019, which is incorporated in its entirety into this application.

SUMMARY

Briefly summarized, embodiments disclosed herein are directed to needle shields for use with ultrasound ("U/S") probe head to protect the ultrasound transducer and any associated structures from accidental damage from a needle.

Ultrasound imaging systems are used to facilitate vascular access under ultrasound image guidance. To improve acoustic communication between the transducer located in the ultrasound probe head and the skin surface of the patient, the probe head often includes various additional structures, for example covers, hydrogel spacers, and the like. Such structures are optimized for conveying acoustic energy and as such, are not necessarily formed of materials that are resistant to damage from accidental needle sticks. Needles for accessing the vasculature are inserted adjacent to the position of the ultrasound probe head as it is held against the skin surface of the patient. This is often performed while the clinician is observing a console or display disposed remotely from the insertion site. Accordingly, there is a risk that the needle can be accidentally inserted into the probe head, or associated structures, causing significant damage to the probe head, transducer, or associated structures.

Disclosed herein is an ultrasound system, comprising a probe, including a body and a probe head, and a needle shield that engages a portion of the probe head, securing the needle shield thereto, the needle shield including one or more side portions formed as a single structure and defining a thickness of between 1 mm-5 mm, the needle shield being formed of a first material that is needle impenetrable and defines a first acoustic impedance.

In some embodiments, the needle shield comprises an acoustic surface cover disposed over an acoustic surface of the probe head, a first lateral side extending from the acoustic surface cover and engages a first lateral side surface of the probe head, and a second lateral side extending from the acoustic surface opposite the first lateral side surface and engages a second lateral side surface of the probe head.

In some embodiments, the needle shield comprises an acoustic surface cover disposed over an acoustic surface of the probe head, a first lateral side extending from the acoustic surface cover and engages a first lateral side surface of the probe head, a second lateral side extending from the acoustic surface opposite the first lateral side surface and engages a second lateral side surface of the probe head, a first transverse side extending from the acoustic surface cover and engages a first transverse side surface of the probe head, and a second transverse side extending from the acoustic surface opposite the first transverse side surface and engages a second transverse side surface of the probe head. The needle shield further includes an aperture disposed in the acoustic surface cover, the aperture exposing a portion of the acoustic surface of the probe head to a skin surface of the patient.

In some embodiments, the needle shield comprises an acoustic surface cover disposed over an acoustic surface of the probe head, a first transverse side extending from the acoustic surface cover and engages a first transverse side surface of the probe head, and a second transverse side extending from the acoustic surface opposite the first transverse side surface and engages a second transverse side surface of the probe head.

In some embodiments, the needle shield is secured to the probe head by one of mechanical interference, a protrusion and detent engagement, a protrusion and aperture engagement, and adhesive. The needle shield further includes a guide wedge disposed on a side portion of the one or more side portions, and includes a guide surface that contacts a skin surface of the patient. The guide surface is angled relative to an acoustic surface of the probe head so that the probe extends longitudinally at a predetermined angle relative to a vertical axis. The predetermined angle is 20°. The guide surface includes an acoustic lens. The acoustic lens is formed of a second material that defines a second acoustic impedance.

Also disclosed herein is a method of accessing a vasculature of a patient under ultrasonic image guidance, the method comprising providing a needle, an ultrasound imaging system, including an ultrasound probe, the probe including a body and a probe head, and a needle shield configured to engage a portion of the probe head, the needle shield including one or more side portions and a guide wedge, the needle shield being formed of a first material that is needle impenetrable and defines a first acoustic impedance. Urging to the needle shield onto the probe head, imaging a subcutaneous portion of a patient to identify a target vessel by resting a guide surface of the guide wedge against a skin surface of the patient so that a longitudinal axis of the probe is at a predetermined angle relative to a vertical axis extending perpendicular to the skin surface of the patient, and accessing the target vessel with the needle by penetrating the skin surface parallel to the vertical axis.

In some embodiments, the needle shield includes an acoustic lens that modifies a direction of an acoustic beam from the probe head, to align with the vertical axis. The acoustic lens includes a concave structure disposed in the guide surface of the guide wedge. The acoustic lens includes a second material, defining a second acoustic impedance, disposed in the guide surface of the guide wedge. The predetermined angle is between 0° and 45° from the vertical axis. The predetermined angle is 20° from the vertical axis.

These and other features of the concepts provided herein will become more apparent to those of skill in the art in view of the accompanying drawings and following description, which disclose particular embodiments of such concepts in greater detail.

DRAWINGS

DESCRIPTION

Figure 1A:
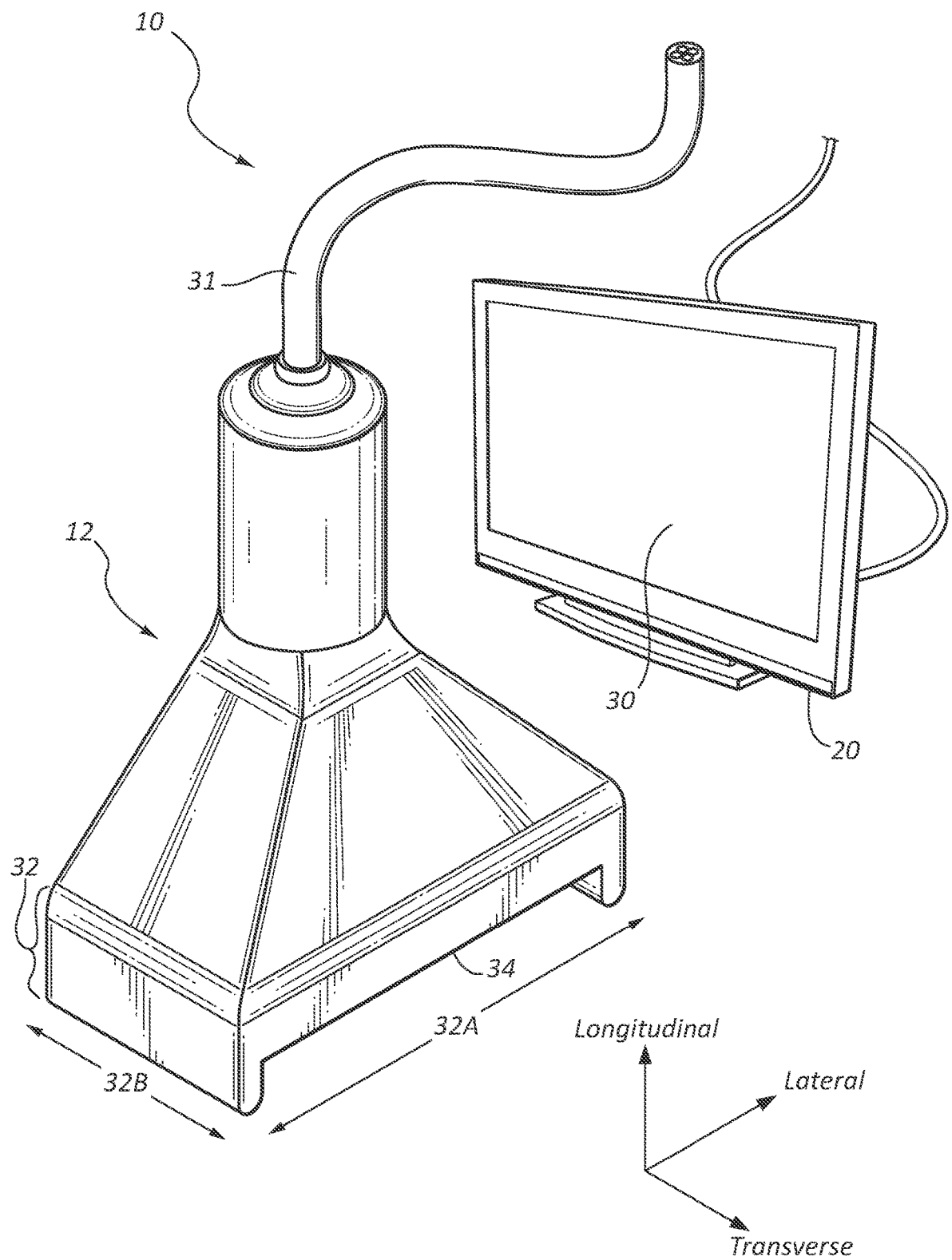
FIG. 1A illustrates an exemplary ultrasound system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

As shown in FIG. 1A, and to assist in the description of the components of embodiments described herein, the probe is described in terms of being held vertically with an acoustic surface being held against a horizontal surface. The longitudinal axis extends perpendicular to the acoustic surface. The acoustic surface is defined by the lateral and transverse axes, with the lateral axis extending normal to the longitudinal axis, and the transverse axis extending normal to both the lateral and longitudinal axis. Unless defined otherwise, all technical and scientific terms used herein have the same meaning as commonly understood by those of ordinary skill in the art.

Figure 1B:
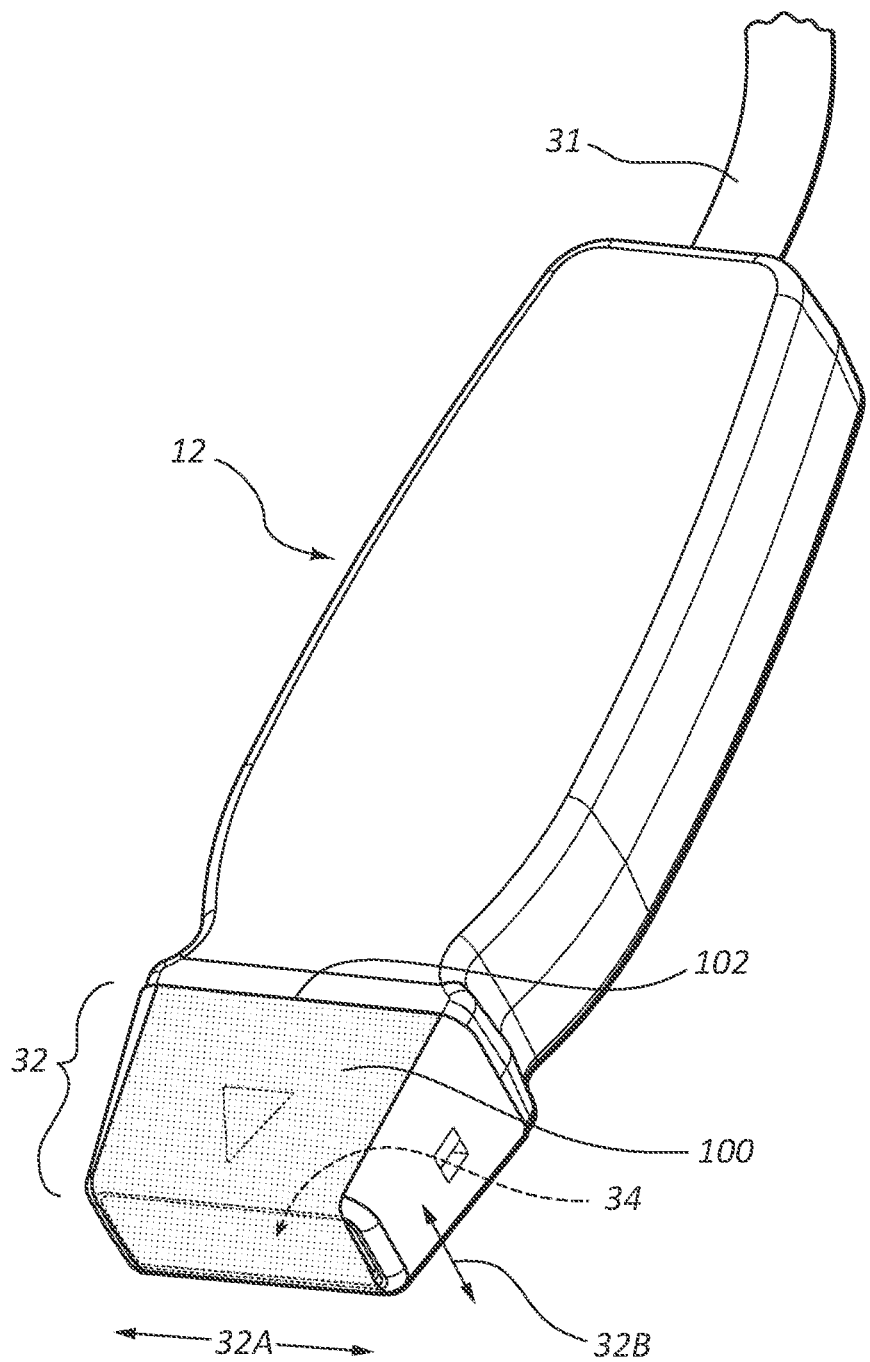
FIG. 1B illustrates an exemplary ultrasound probe including a needle shield, in accordance with embodiments disclosed herein.

FIGS. 1A-1B show exemplary embodiments of an ultrasound imaging system 10 that generally includes an ultrasound probe 12 and a console 20 including a display 30 for depicting an image produced by the probe 12. In an embodiment, the probe 12 is operably connected to the console 20 via a cable 31, though in an embodiment the probe can be wirelessly connected thereto.

The probe 12 includes a head portion ("probe head," or "head") 32 defined by a lateral length 32A and a transverse width 32B. The head 32 includes an acoustic surface 34 extending along at least a portion of a lateral length 32A of the probe head from which ultrasonic impulses are emitted by a transducer, disposed within the probe head 32, in order to penetrate and image subcutaneous portions of the patient. Note that the size, shape and configuration of both the probe 12, probe head 32, transducer, and acoustic surface 34 can vary from what is described herein while still residing within the principles of the present disclosure. Note also that FIGS. 1A-1B show exemplary ultrasound imaging systems; other systems including other components can also benefit from the principles described herein.

As shown in FIG. 1B, the probe head 32 can further include a needle shield 100. The needle shield 100 can be coupled with the probe head 32, or portions thereof and cover a portion of the probe head 32. In an embodiment, the needle shield 100 is formed of a resilient material that is resistant to penetrations from a needle. In an embodiment, the needle shield 100 is formed of a material that is transparent to acoustic energy passing through the needle shield 100, either as transmitted energy from the transducer, or as reflected energy received by the transducer.

In an embodiment, the needle shield 100 is formed of a resilient material such as plastic, polymer, metal, or the like that is resistance to penetration from a needle and is substantially rigid. The needle shield 100 defines a substantially uniform thickness of between 0.25 mm to 5 mm, for example 1 mm. The needle shield conforms to the outer profile of the probe head 32 and any associated covers, spacers, and the like to provide a protective layer thereover. As used herein, the needle shield is described as co-operating with the probe head 32. However, it will be appreciated that the probe head can further include various covers, needle guides, spacers, and other additional structures. Accordingly, the needle shield 100 can be formed to co-operate with both the probe head and these additional structures, forming a protective barrier thereover.

In an embodiment, the needle shield 100 is coupled with the probe head 32 and secured thereto through mechanical interference against the probe head 32. For example, as shown in FIGS. 1B, 2A-2D, a first lateral proximal edge 102 of the needle shield 100 co-operates with a concave portion of the probe head 32. Further, while the needle shield is formed of a substantially rigid material, there is sufficient flexibility so that the proximal edge 102 can be urged over the probe head 32 and clipped into place, securing the needle shield 100 thereto. As shown in FIG. 3, a second lateral proximal edge 106, opposite the first lateral proximal edge 102, provides an opposing force and secures the needle shield 100 to the probe head 32.

Figures 2A, 2B:
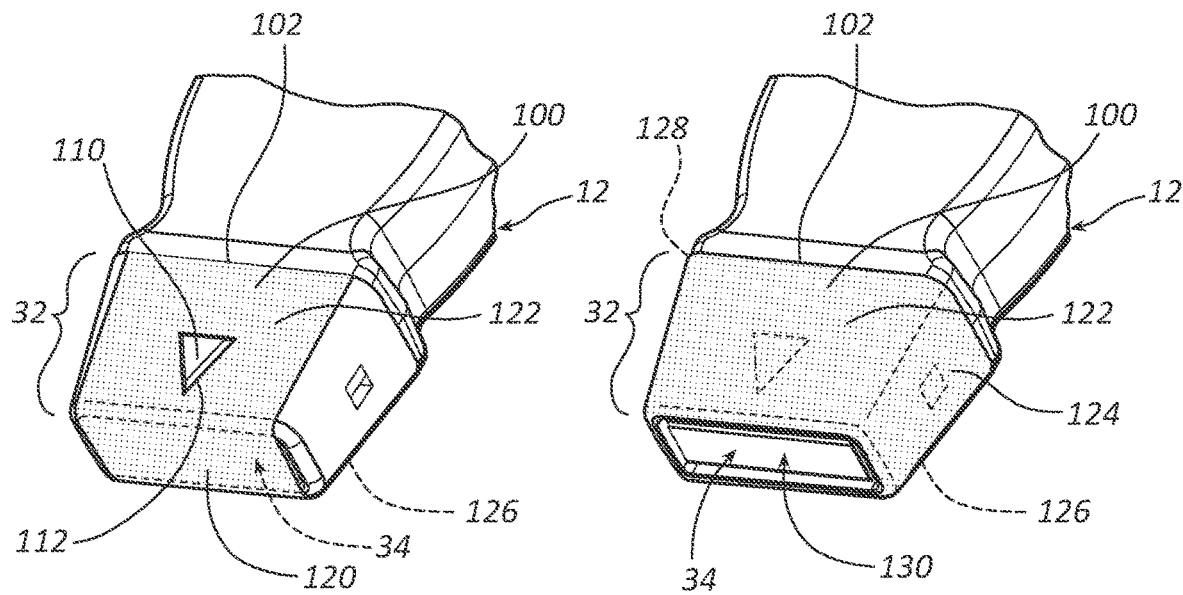
FIGS. 2A-2D illustrates an ultrasound probe head including exemplary embodiments of a needle shield, in accordance with embodiments disclosed herein.
Figures 2C, 2D:
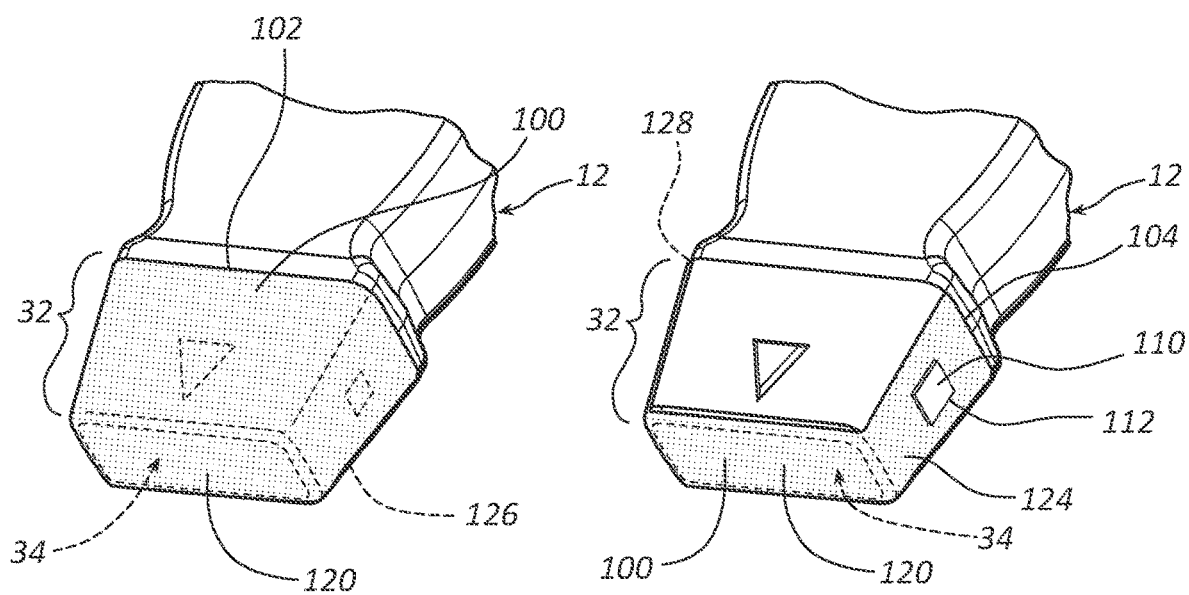

In an embodiment, the needle shield 100 is coupled with probe head 32 and secured thereto by way of an interengaging protrusion and detent. As shown in FIGS. 2A, 2D, the probe head 32 includes one or more protrusions 110, guide hooks, or similar protruding structures, disposed on a surface of the probe 12, probe head 32, or combinations thereof. The needle shield 100 includes one or more detents 112, apertures, or combinations thereof, which engage the one or more protrusions 110 to secure needle shield 100 thereto. As described herein, while the needle shield 100 is formed of a substantially rigid material, there is sufficient flexibility so that needle shield 100 can be urged over the protrusions 110 disposed on the probe head 32 so that corresponding detents 112, apertures, and the like, can engage the protrusions 110 and secure the needle shield 100 to the probe head 32. While the embodiment has been described with the protrusion 110 disposed on the probe head 32, it will be appreciated that the protrusion 110 can be disposed on needle shield 100, the probe head 32, or combinations thereof, without departing from the spirit of the invention. Similarly, the aperture/detent 112 can be disposed on the probe head 32, needle shield 100, or combinations thereof, without departing from the spirit of the invention.

In an embodiment, the needle shield 100 is coupled with the probe head 32 and secured thereto using an adhesive layer disposed between the needle shield 100 and the probe head 32.

FIGS. 2A-2D show various embodiments of the needle shield 100. As shown in FIG. 2A, in an embodiment, the needle shield 100 includes an acoustic surface cover portion 120, which covers the acoustic surface 34 of the probe head. Extending from the acoustic surface cover portion 120 is a first lateral side portion 122 and a second lateral side portion 126, which extend over respective lateral sides of the probe head 32.

As shown in FIG. 2B, in an embodiment, the needle shield 100 includes a first lateral side portion 122, a second lateral side portion 126, a first transverse side portion 124 and a second transverse side portion 128 that extend over respective lateral and transverse sides of the probe head 32. The needle shield 100 further includes an aperture 130 that aligns with the acoustic surface 34.

As shown in FIG. 2C, in an embodiment, the needle shield 100 includes an acoustic surface cover portion 120, which covers the acoustic surface 34 of the probe head. Extending from the acoustic surface cover portion 120 is a first lateral side portion 122, a second lateral side portion 126, a first transverse side portion 124 and a second transverse side portion 128 that extend over respective lateral and transverse sides of the probe head 32.

As shown in FIG. 2D, in an embodiment, the needle shield 100 includes an acoustic surface cover portion 120, which covers the acoustic surface 34 of the probe head. Extending from the acoustic surface cover portion 120 is a first transverse side portion 124 and a second transverse side portion 128, which extend over respective transverse sides of the probe head 32.

Figure 3A:
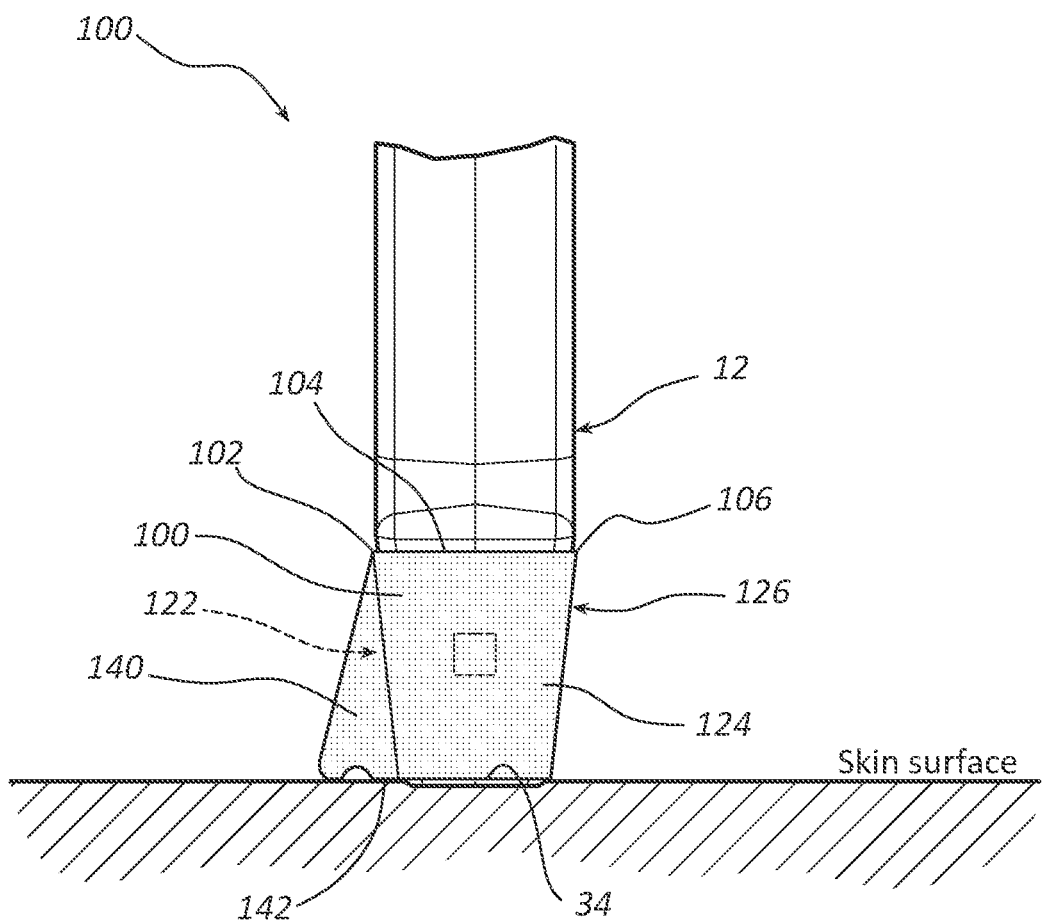
FIG. 3A illustrates a cross sectional view of an ultrasound probe including an exemplary needle shield, in accordance with embodiments disclosed herein.
Figure 3B:
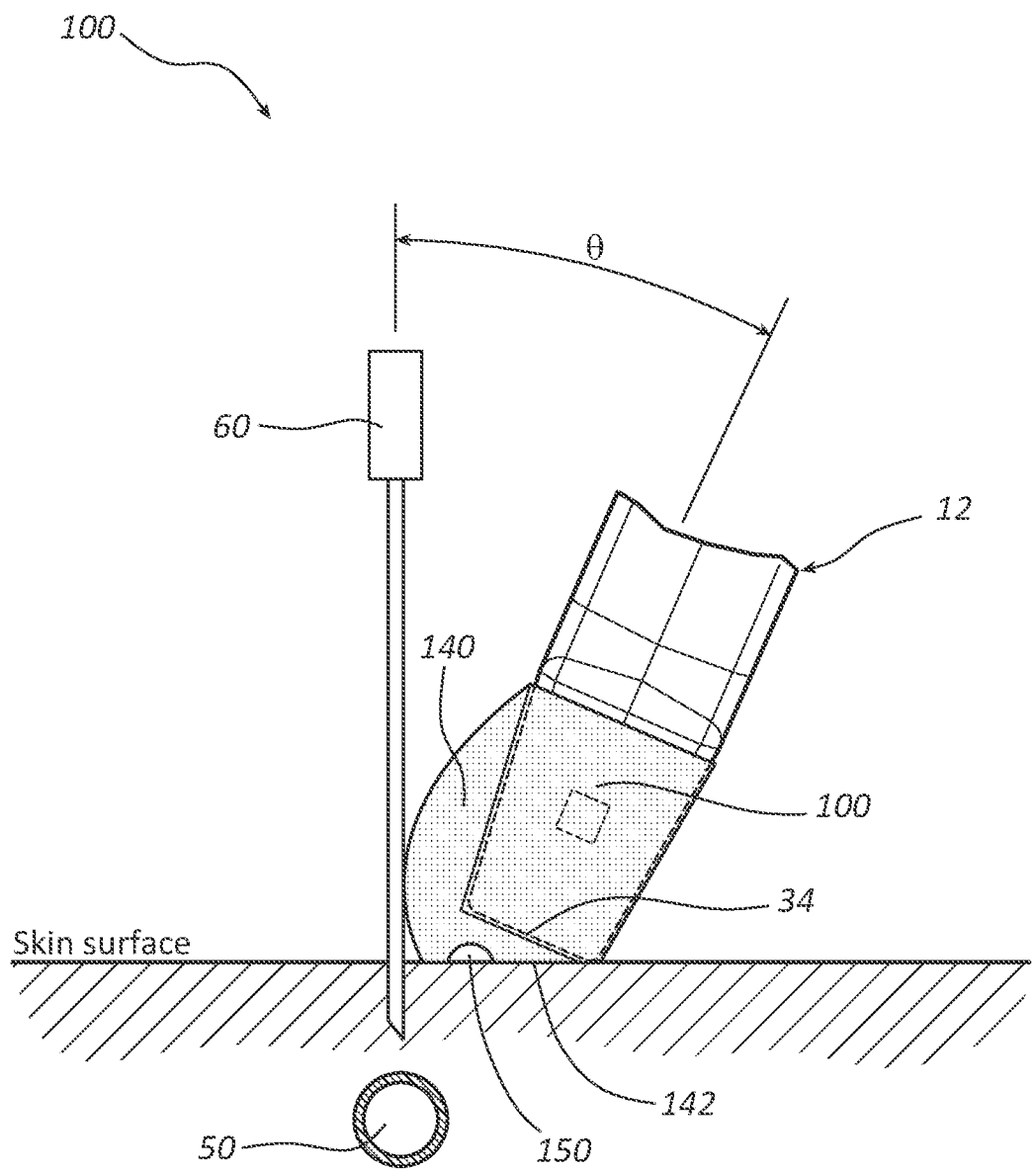
FIG. 3B illustrates a cross sectional view of an ultrasound probe including an exemplary needle shield, in accordance with embodiments disclosed herein.

As shown in FIGS. 3A-3B, in an embodiment the needle shield 100 further includes a guide wedge 140. The guide wedge 140 includes a portion of the needle shield that defines a greater thickness than the rest of the needle shield 100, and a smooth, outer profile that is continuous with that of the outer profile of the needle shield 100. A guide surface 142 of the guide wedge 140 aligns with the skin surface of the patient and is angled relative to the acoustic surface 34 to support the probe 12 at a predetermined angle. For example, as shown in FIG. 3A, the guide surface 142 is substantially parallel with the acoustic surface 34 and supports the probe 12 in a substantially vertical orientation. As shown in FIG. 3B, the guide surface 142 can be angled relative to the acoustic surface 34 and supports the probe at a predetermined angle "θ" relative to the vertical axis, extending perpendicular to the skin surface of the patient. The predetermined angle "θ" can be between 0° and 45° from the vertical axis, for example about 20° from the vertical axis.

Advantageously, the guide wedge 140 can support the probe 12 so that it does not obstruct access to the vessel 50. Many procedures require the vessel to be accessed perpendicular to the skin surface, however, most ultrasound transducers are designed to also be held perpendicular to the skin surface, obstructing access to the vessel 50. Accordingly, the needle shield 100, including the guide wedge 140 can position the probe to one side, while maintaining a steady angle. Optionally, the probe head 32 can further include a needle guide or similar structures.

In an embodiment, the needle shield includes an acoustic lens 150 that focusses the energy emitted from the transducer to a predetermined focal point. As shown in FIG. 3B, the probe 12 can be angled relative to the skin surface to allow a needle 60 to access the vessel 50 perpendicular to the skin surface. As such, the direction of the acoustic beam emanating from the transducer is also angled with respect to the skin surface. These angled beams can impede the clarity and accuracy of the ultrasound system 10 by introducing refractive or deflective elements to the beam characteristic at the skin surface. Accordingly, the needle shield 100 includes an acoustic lens 150 disposed on the guide surface 142 to correct for the angled position of the probe 12 relative to the skin surface.

In an embodiment, the needle shield 100 can be formed of a single material and the acoustic lens 150 can include a concave structure disposed on the guide surface. In an embodiment, acoustic lens includes a portion of a second material, different from that of a first material that forms the needle shield 100. For example, the needle shield can be formed of a first, rigid material that defines a first acoustic impedance and the acoustic lens includes portion of a second material, which defines a second acoustic impedance. It will be appreciated, that the size, shape, location, and number of acoustic lenses can vary from what is shown and still fall within the scope of the present invention. Further the acoustic impedance of the first material, can be greater than, or less than, the acoustic impedance of the second material and still fall within the scope of the present invention.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound system, comprising:
 a probe, including a body and a probe head having:
  an acoustic surface;
  a first lateral side surface;
  a second lateral side surface opposite the first lateral side surface;
  a first transverse side surface; and
  a second transverse side surface opposite the first transverse side surface;
 a cover covering the probe head; and
 a flexible needle shield conforming to an outer profile of both the probe head and the cover, the needle shield including one or more side portions formed as a single structure having a thickness of between 0.25 mm-1 mm, and the needle shield being formed of at least a first material that is capable of resisting penetration by a needle, thereby shielding at least the probe head and the cover from accidental needle damage, wherein at least one of the one or more side portions:
extends entirely across the first lateral side surface, the second lateral side surface, the first transverse side surface, or the second transverse side surface; and includes a uniform thickness.

2. The ultrasound system of claim 1, wherein the probe head includes a spacer to improve acoustic communication between a transducer located in the probe head and a skin surface of a patient; and wherein the needle shield further includes an aperture configured to align with the acoustic surface.

3. The ultrasound system of claim 1, wherein the needle shield is secured to the outer profile of both the probe head and the cover by an adhesive.

4. The ultrasound system of claim 1, wherein a portion of the needle shield extends over the acoustic surface to define an acoustic surface cover.

5. The ultrasound system of claim 4, wherein the one or more side portions of the needle shield include:
a first lateral side extending from the acoustic surface cover over the first lateral side surface; and
a second lateral side extending from the acoustic surface over the second lateral side surface.

6. The ultrasound system of claim 5, wherein the one or more side portions of the needle shield further include:
a first transverse side extending from the acoustic surface cover over the first transverse side surface; and
a second transverse side extending from the acoustic surface cover over the second transverse side surface.

7. The ultrasound system of claim 4, wherein the one or more side portions of the needle shield include:
a first transverse side extending from the acoustic surface cover over the first transverse side surface; and
a second transverse side extending from the acoustic surface over the second transverse side surface.

8. The ultrasound system of claim 1, wherein the first material is a polymer capable of resisting penetration by the needle at the thickness of between 0.25 mm-1 mm.

9. The ultrasound system of claim 8, wherein the needle shield is secured to the outer profile of both the probe and the cover by an adhesive.

10. The ultrasound system of claim 1, wherein the needle shield further includes a guide wedge coupled to the needle shield, the guide wedge including:
a guide surface configured to engage a skin surface and support the acoustic surface of the probe head at an acute angle relative to the skin surface; and
an acoustic lens disposed on the guide surface to modify an angle of an acoustic beam from the acoustic surface of the probe head.

11. The ultrasound system of claim 10, wherein the guide wedge is disposed on a side portion of the one or more side portions of the needle shield.

12. The ultrasound system of claim 11, wherein the guide surface is angled relative to the acoustic surface of the probe head so that the probe extends longitudinally at a predetermined angle of 20° relative to a vertical axis.

13. The ultrasound system of claim 10, wherein the acoustic lens is formed of a second material that defines a second acoustic impedance different than a first acoustic impedance of the first material.

14. An ultrasound system, comprising:
a probe including a probe body and a probe head having an acoustic surface;
a cover covering the probe head; and
a flexible needle shield conforming to an outer profile of both the probe head and the cover, the needle shield including one or more side portions adhered to the outer profile of the probe head and the cover by an adhesive layer of the needle shield, the needle shield formed of a polymer in a single structure having a uniform thickness between 0.25 mm-1 mm, thereby shielding at least the probe head and the cover from accidental needle damage.

15. The ultrasound system of claim 14, wherein the needle shield includes an acoustic surface cover defined by a portion of the needle shield extending over the acoustic surface of the probe head; a first lateral side extending from the acoustic surface cover over a first lateral side surface of the probe head; and a second lateral side opposite the first lateral side surface, the second lateral side extending from the acoustic surface cover over a second lateral side surface of the probe head.

16. The ultrasound system of claim 15, wherein the needle shield further includes a first transverse side extending from the acoustic surface cover over a first transverse side surface of the probe head; and a second transverse side opposite the first transverse side surface, the second transverse side extending from the acoustic surface cover over a second transverse side surface of the probe head.

17. The ultrasound system of claim 16, wherein the needle shield extends entirely across:
the first transverse side surface of the probe head to define the first transverse side, and
the second transverse side surface of the probe head to define the second transverse side.

18. The ultrasound system of claim 14, wherein the needle shield includes an acoustic surface cover defined by a portion of the needle shield extending over the acoustic surface of the probe head; a first transverse side extending from the acoustic surface cover over a first transverse side surface of the probe head; and a second transverse side opposite the first transverse side surface, the second transverse side extending from the acoustic surface cover over a second transverse side surface of the probe head.

19. The ultrasound system of claim 14, wherein the probe head includes a spacer to improve acoustic communication between a transducer located in the probe head and a skin surface of a patient; and wherein the needle shield includes an aperture configured to align with the acoustic surface of the probe head; a first lateral side extending from the aperture over a first lateral side surface of the probe head; and a second lateral side opposite the first lateral side surface, the second lateral side extending from the aperture over a second lateral side surface of the probe head.

20. The ultrasound system of claim 19, wherein the needle shield further includes a first transverse side extending from the aperture over a first transverse side surface of the probe head; and a second transverse side opposite the first transverse side surface, the second transverse side extending from the aperture over a second transverse side surface of the probe head.

21. The ultrasound system of claim 14, wherein the probe head includes a spacer to improve acoustic communication between a transducer located in the probe head and a skin surface of a patient; and wherein the needle shield includes an aperture configured to align with the acoustic surface of the probe head; a first transverse side extending from the aperture over a first transverse side surface of the probe head; and a second transverse side opposite the first transverse side surface, the second transverse side extending from the aperture over a second transverse side surface of the probe head.

* * * * *